US009127045B2

(12) United States Patent
Goodman et al.

(10) Patent No.: US 9,127,045 B2
(45) Date of Patent: Sep. 8, 2015

(54) METHOD OF INHIBITING BACTERIAL GROWTH AND BIOFILM FORMATION WITH NATURAL QUORUM SENSING PEPTIDES

(75) Inventors: Steven D. Goodman, Redondo Beach, CA (US); Olga Kay, Los Angeles, CA (US); Wenyuan Shi, Los Angeles, CA (US); Fengxia Qi, Oklahoma City, OK (US)

(73) Assignees: UNIVERSITY OF SOUTHERN CALIFORNIA, Los Angeles, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 2041 days.

(21) Appl. No.: 11/561,275

(22) Filed: Nov. 17, 2006

(65) Prior Publication Data

US 2008/0069782 A1 Mar. 20, 2008

Related U.S. Application Data

(60) Provisional application No. 60/738,361, filed on Nov. 17, 2005.

(51) Int. Cl.
C07K 14/00 (2006.01)
A61K 8/60 (2006.01)
A61Q 11/00 (2006.01)
A61Q 17/00 (2006.01)
C12N 1/00 (2006.01)

(52) U.S. Cl.
CPC . *C07K 14/00* (2013.01); *A61K 8/60* (2013.01); *A61Q 11/00* (2013.01); *A61Q 17/005* (2013.01); *C12N 1/00* (2013.01)

(58) Field of Classification Search
CPC .................................................. C07K 14/00
USPC ......................................... 530/326; 514/21.4
See application file for complete search history.

(56) References Cited

U.S. PATENT DOCUMENTS

| 4,692,407 | A | 9/1987 | Jordan et al. |
| 4,725,576 | A | 2/1988 | Pollock et al. |
| 5,013,542 | A | 5/1991 | Hay et al. |
| 5,374,538 | A | 12/1994 | Bratthalli |
| 5,486,503 | A | 1/1996 | Oppenheim et al. |
| 5,631,228 | A | 5/1997 | Oppenheim et al. |
| 5,646,119 | A | 7/1997 | Oppenheim et al. |
| 5,801,226 | A | 9/1998 | Cummins et al. |
| 5,807,541 | A | 9/1998 | Aberg et al. |
| 5,830,489 | A | 11/1998 | Valenti et al. |
| 5,885,965 | A | 3/1999 | Oppenheim et al. |
| 5,912,230 | A | 6/1999 | Oppenheim et al. |
| 6,024,958 | A * | 2/2000 | Lehner et al. ............. 424/190.1 |
| 6,136,298 | A | 10/2000 | Gaffar et al. |
| 6,231,857 | B1 | 5/2001 | Shi et al. |
| 6,923,962 | B2 | 8/2005 | Cvitkovitch et al. ...... 424/164.1 |
| 7,087,228 | B2 | 8/2006 | Goodman et al. |
| 2002/0081302 | A1 | 6/2002 | Cvitkovitch et al. |

OTHER PUBLICATIONS

Ellen, R.P., "Microbiological Assays for Dental Caries and Periodontal Disease Susceptibility," Oral Sci. Rev., 1976, vol. 8; pp. 3-23.
Fukushima, K., et al., "Production Characterization and Application of Monoclonal Antibodies which Distinguish Three Glucosyltransferases from *Streptococcus* Mutans," Infection and Immunity, 1993, vol. 61; pp. 323-328.
Goodman, et al., "Firefly Luciferase as a Reporter to Study Gene Expression in *Streptococcus* Mutans," Plasmid, 1999, vol. 42; pp. 154-157.
Goodman, et al.,"Characterization of the gtfB and gtfC Promoters from *Streptococcus* Mutans GS-5," Plasmid, 2000, vol. 43; pp. 85-98.
Goodman, et al. "In Vitro Selection of Integration Host Factor Binding Sites," J. of Bact., 1999, vol. 81, pp. 2346-3255.
Hanada, et al., "Isolation and Characterization of the *Streptococcus* Mutans gtfD Gene Coding for Primer-Dependent Soluble Glucan Synthesis," Infection and Immunity, 1989, vol. 57; pp. 2079-2085.
Hume, "Need for Change in Standards of Caries Diagnosis-Perspective Based on the Structure and Behavior of the Carious Lesion," J. Dent. Educ. 1993, vol. 57; pp. 439-443.
Idone, et al., "Effect of an Orphan Response Regulator on *Streptococcus* Mutans Sucrose-Dependent Adherence and Cariogenesis," Infection and Immunity, 2003; vol. 71(8); pp. 4351-4360.
Igarashi, et al., "Direct Detection of *Streptococcus* Mutans in Human Dental Plaque by Polymerase Chain Reaction," Oral Microbiol and Immunol. 1996, vol. 11; pp. 294-298.
Keys, "Infective Endocartitis," The Cleveland Clinic, 2004, pp. 1-12.
Kumar, et al., "Amino Acid Variations at a Single Residue in an Autoimmune Peptide Profoundly Affect its Properties: T-Cells Activation," Immunology, 1990; vol. 87, pp. 1337-1341.
Kuramitsu, et al., "Immunological Relationships Between Glucosyltransferase from *Streptococcus* Mutans Serotypes," Infection and Immunity, 1976, vol. 14(3); pp. 636-644.
Kuramitsu, T.H., "The role of the *Streptococcus* mutans glucosyltransferases in the sucrose-dependent attachment to smooth sufaces: essential role of the GtfC enzyme," Oral Microbiology and Immunology, vol. 12; pp. 274-280.
Lee, et al., "Identification of a New Regulator in *Streptococcus pneumociae* Linking Quorum Sensing to Competence for Genetic Transformation," J. of Bact., 1999, vol. 181; pp. 5004-5016.

(Continued)

Primary Examiner — David Lukton
(74) Attorney, Agent, or Firm — DLA Piper LLP (US)

(57) ABSTRACT

Methods for selectively manipulating a growth rate of a selected bacterium comprising the step of contacting the selected bacterium with a predetermined amount of a quorum sensing molecule to affect a change in the growth rate of the selected bacterium, wherein the quorum sensing molecule is species specific, and the change in the growth rate is dependent on the amount of quorum sensing molecule in a dose-dependent fashion. Also provided are methods for treating or protecting against bacterial infections by utilizing the dose-dependent response of bacterial quorum sensing systems. The methods can be applied to a wide range of bacteria species including *Streptococci*, *Staphylococci*, and *Bacilli*. Compositions, medicaments and oral formulations for use with the methods are also disclosed.

18 Claims, 12 Drawing Sheets

(56) References Cited

OTHER PUBLICATIONS

Lenander-Lumikari, et al., "Saliva and Dental Caries," Adv. Dent. Res., 2000, vol. 14; pp. 40-47.

Li, et al., "Natural Genetic Transformation of *Streptococcus* Mutans Growing in Biofilms," J. of Bac., 2001, vol. 183; pp. 897-908.

Lowry, R.J. et al., "Hearts and mouths: perceptions of oral hygiene by at-risk heart surgery patients," British Dental Journal, vol. 199(7); pp. 449-451.

Nosoh, et al., "Protein and Stabilization through Protein Engineering," 1991, Chapter 7, p. 197, $2^{nd}$ Paragraph.

Ooshima, et al., Carlostatic Activity of Cacao Mass Extract, *Archives of Oral Biology*, 2000, vol. 45(9), pp. 805-808.

Prabhu, R.M., et al., "Antimicrobial Susceptibility Patterns among Viridans Group *Streptococcal* Isolates from Infective Endocarditis Patients from 1971 to 1986 and 1994 to 2002," Antimicrobial Agents and Chemotherapy, 2004, vol. 48(11); pp. 4463-4465.

Schelenz, S. et a., "*Streptococcus* mutans endocarditis: beware of the 'diphtheroid'", Journal of the Royal Society of Medicine, 2005, vol. 98; p. 420.

Seki, M., et al., "Evaluation of mutans streptococci in plaque and saliva: correlation with caries development in preschool children," Journal of Dentistry, 2003, vol. 31; pp. 283-290.

Stenudd, C., et al., "The Association of Bacterial Adhesion With Dental Caries," J Dent Res, 2001, vol. 80(11); pp. 2005-2010.

Tanzer, "Understanding Dental Caries; an Infectious Disease, not a Lesion," Inter. J. Oral Biol. 1997, vol. 22; pp. 205-214.

Zero, Sugars, "The Arch Criminal," Caries Research, 2004; vol. 38, pp. 277-285.

Senadheera, et al., Journal of Bacteriology, "A VicRK Signal Transduction System in *Streptococcus* Mutans Affects gtfBCD, gbpB, and ftf Expression, Biofilm Formation, and Genetic Competence Development," Jun. 2005, pp. 4064-4076.

Qi et al FEMS Microbiology Letters, "Peptide Pheromone Induced Cell Death of *Streptococcus* Mutans," (2005), pp. 321-326.

\* cited by examiner

SGSLSTFFRLFNRSFTQALGK    (SEQ ID NO:1)

Figure 2

CSP added: none 5 mcg/ml

Panel 1: anti-*gtf* (glucosyltransferase) antibody

Panel 2: anti-*ftf* (fructosyltransferase) antibody

```
                    -11
                     |
        gtfB    ACAATTATAACGTTTTGAATAAA*ACAGTTTAA
                ||| ||    |  ||||  ||||||  |||||| |
     ComE Box   aCAtTTcRGWWWWWWWWWWWWWWW*ACAGTTgAG
                ||| | |    | ||||||||| ||  ||| |
        gtfC    ACAATACTAGTGTTTTATATCAAAACACTAACT
```

METHOD OF INHIBITING BACTERIAL GROWTH AND BIOFILM FORMATION WITH NATURAL QUORUM SENSING PEPTIDES

CROSS-REFERENCE TO RELATED APPLICATIONS

This application claims priority, pursuant to 35 U.S.C. §119(e), to U.S. Provisional Application Ser. No. 60/738,361 filed on Nov. 17, 2005, the content of which is incorporated herein in its entirety.

FIELD OF THE INVENTION

The present invention generally relates to methods for manipulating bacterial growth using a quorum sensing molecule. In particular, the present invention provides methods for the selective inhibition of bacterial growth in a biofilm. The present invention also relates to methods of treating or protecting against dental caries and infective endocarditis.

BACKGROUND OF THE INVENTION

A biofilm is a complex aggregation of microorganisms marked by the secretion of a protective and adhesive matrix. Biofilms are also often characterized by surface attachment, structural heterogeneity, genetic diversity, complex community interactions, and an extracellular matrix of polymeric substances.

Single-celled organisms generally exhibit two distinct modes of behavior. The first is the familiar free floating, or planktonic, form in which single cells float or swim independently in some liquid medium. The second is an attached state in which cells are closely packed and firmly attached to each other and usually a solid surface. The change in behaviour is triggered by many factors, including quorum sensing, as well as other mechanisms that vary between species. When a cell switches modes, it undergoes a phenotypic shift in behavior in which large suites of genes are up- and down-regulated.

Biofilms are usually found on solid substrates submerged in or exposed to some aqueous solution, although they can form as floating mats on liquid surfaces. Given sufficient resources for growth, a biofilm will quickly grow to be macroscopic. Biofilms can contain many different types of microorganisms, e.g. bacteria, archaea, protozoa and algae; each group performing specialized metabolic functions. However, some organisms will form monospecies films under certain conditions.

The biofilm is held together and protected by a matrix of excreted polymeric compounds called EPS. EPS is an abbreviation for either extracellular polymeric substance or exopolysaccharide. For the purpose of this application, EPS will mean exopolysaccharide. This matrix protects the cells within it and facilitates communication among them through biochemical signals. Some biofilms have been found to contain water channels that help distribute nutrients and signalling molecules. This matrix is strong enough that under certain conditions, biofilms can become fossilized.

Bacteria living in a biofilm usually have significantly different properties from free-floating bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community. In some cases antibiotic resistance can be increased 1000 fold (Stewart and Costerton 2001).

Biofilms are ubiquitous. Nearly every species of microorganism, not only bacteria and archaea, have mechanisms by which they can adhere to surfaces and to each other.

Biofilms can be found on rocks and pebbles at the bottom of most streams or rivers and often form on the surface of stagnant pools of water. Biofilms are important components of food chains in rivers and streams and are grazed by the aquatic invertebrates upon which many fish feed.

Biofilms grow in hot, acidic pools in Yellowstone National Park (USA) and on glaciers in Antarctica.

In industrial environments, biofilms can develop on the interiors of pipes, which can lead to clogging and corrosion. Biofilms on floors and counters can make sanitation difficult in food preparation areas.

Biofilms can also be harnessed for constructive purposes. For example, many sewage treatment plants include a treatment stage in which waste water passes over biofilms grown on filters, which extract and digest organic compounds. In such biofilms, bacteria are mainly responsible for removal of organic matter (BOD); whilst protozoa and rotifers are mainly responsible for removal of suspended solids (SS), including pathogens and other microorganisms. Slow sand filters rely on biofilm development in the same way to filter surface water from lake, spring or river sources for drinking purposes.

One widely recognized health problem associated with biofilms is that they are present on the teeth of most animals, where they may become responsible for tooth decay.

In addition to tooth decay, biofilms have also been found to be involved in a wide variety of microbial infections in the body, by one estimate 80% of all infections (NIH 2002). Infectious processes in which biofilms have been implicated include common problems such as urinary tract infections, catheter infections, middle-ear infections, gingivitis, coating contact lenses, and less common but more lethal processes such as endocarditis, infections in cystic fibrosis, and infections of permanent indwelling devices such as joint prostheses and heart valves. (Lewis 2001, Parsek and Singh 2003).

Such bacterial infections are a persistent problem in human health. Outside of the body there are several means used to control reservoirs of infection including chemical disinfectants and forms of high-energy electromagnetic radiation e.g. ultraviolet light and X-rays. Although effective at controlling environmental populations, they cannot be used to treat bacterial pathogens once infection has occurred. To date, the only treatment that is known to be effective is antibiotics. The way antibiotics generally works is to take advantage of the variant metabolic pathways that exist between humans and bacteria, thereby, differentially affecting bacterial cells. They have two big drawbacks. First, they are not specific against any one type of bacteria and can damage commensal or beneficial bacteria resulting in new pathologies. Second, bacteria have readily evolved to become resistant to antibiotics. Since antibiotics are not beneficial to the bacteria, they can be neutralized without a loss of any critical functions. In addition, antibiotics are not very effective against a bacterial infection that has formed a biofilm.

Therefore, there still exists a need for an improved method to treat biofilm-related bacterial infections as well as to manage the formation of biofilms.

SUMMARY OF THE INVENTION

The present invention is based on the unexpected discovery that the growth rate of bacterial cells has a dose-dependent response to quorum sensing molecules, and that at high dosages, the quorum sensing molecules actually induce cell death. Based on this discovery, and the knowledge that some quorum sensing molecules are species specific, a method for manipulating a selected bacterial population is developed in the present invention.

Accordingly, in one aspect, the present invention provides a method for selectively manipulating a growth rate of the selected bacterium, comprising the step of contacting the selected bacterium with a predetermined amount of a quorum sensing molecule to effect a change in the growth rate of the selected bacterium, wherein the quorum sensing molecule is species specific, and the change in the growth rate is dependent on the amount of quorum sensing molecule in a dose-dependent fashion.

A method according to this aspect of the present invention may be applied to a wide range of bacterial species including, but not limited to *Streptococci, Staphylococci*, and *Bacilli*. For example, gram-positive bacteria are excellent targets because they have peptide-based, species specific quorum sensing systems.

Although the method of the present invention is a general method that may be applied to a wide range of microbial organisms, in order to facilitate a full and complete understanding of the present invention, the following exemplary discussion of *S. mutans* quorum sensing is provided.

Quorum Sensing (QS)

As used herein, the term "quorum sensing" refers to the ability of bacteria to communicate and coordinate behavior via signaling molecules, or "quorum sensing molecules." Throughout this application, the abbreviations QS and QSM will be used to stand for Quorum Sensing and Quorum Sensing Molecule, respectively.

The purpose of QS is to coordinate certain behaviour or actions between bacteria of the same kind, depending on their number. For example, opportunistic bacteria, such as *Pseudomonas aeruginosa* can grow within a host without harming it, until they reach a certain concentration. Then they become aggressive, their numbers sufficient to overcome the host's immune system and form a biofilm, leading to disease.

QS was first observed in *Vibrio fischeri*, a bioluminiscent bacterium that lives as a symbiont in the light-producing organ of the Hawaiian bobtail squid. When *V. fischeri* cells are free-living, the cells are sparsely distributed and the QSM, also known as the autoinducer, is at low concentration and thus cells do not luminesce. In the light organ of the squid, the cells are highly concentrated (about $10^{11}$ cells/ml) and the QSM alters the gene expression pattern to induce transcription of luciferase, leading to bioluminescence.

Processes possibly regulated or partially regulated by QS systems in *E. coli* include cell division. In other species such as *Pseudomonas aeruginosa* quorum-related processes include biofilm development, exopolysaccharide production, and cell aggregation. *Streptococcus pneumoniae* uses QS to become competent.

Quorum Sensing in *S. mutans*

The bacterium *S. mutans* is one of the primary etiologic agents of tooth decay (Loesche, 1986). These bacteria first adhere to the smooth surface of teeth along with other early colonizing bacteria. Attachment and subsequent growth on the surface is marked by a physiological change where the bacteria undergo a significant alteration in gene regulation to convert from a planktonic (or free living) state to a biofilm (a community adhered to a surface) state. Particularly striking is the formation of extensive structures composed of EPS. Although the bacteria eventually become sessile, the biofilm continues to grow until the structures become so large that they begin to slough off, with the newly planktonic bacteria repeating the biofilm cycle.

One early step in this biofilm formation process is the adherence of *S. mutans* to teeth followed by a dramatic increase in cell density. *S. mutans* has at least two distinct cell-cell communication systems collectively referred to as QS systems. Each QS system shares a general mechanism where the cell secretes an autoinducing molecule. When the population density of the cell and the concentration of the autoinducer reach a critical threshold, the cell can sufficiently bind to and hence sense the autoinducer. The effect of binding is a cascade of changes in gene regulation. Of the two known QS systems, the one that activates competence (the ability to take up new genetic material) is best understood. The current paradigm dictates that once the quorum threshold is achieved, then genes involved in uptake and processing of extracellular DNA (transformation) become activated.

One current model for control of streptococcal competence through QS is outlined in FIG. 1. This system relies in part on a pair of proteins that make up a two component signal transduction system (TCSTS) which relies on a transmembrane sensor and an intracellular response regulator. The pathway is initiated by the expression of the comC gene which encodes a 46 amino acid polypeptide of which the first 25 amino acids represent a signal/secretion domain. This domain is believed to be cleaved off by the ComA/B antiporter that secretes the mature 21 amino acid peptide, henceforth called CSP (competence stimulating peptide). It is believed that when the density of cells and the concentration of CSP reaches a critical threshold, there is sufficient interaction of CSP with the two component transmembrane sensor, ComD. Upon binding of CSP to ComD, the intracellular domain becomes phosphorylated. Consequently, this phosphate group is specifically donated to the ComE response regulator protein. Phosphorylated ComE appears to be able to activate certain promoters by binding to a consensus site −70 to −50 bp upstream of the target genes transcriptional start. All of the aforementioned com genes seem to be upregulated including an additional gene, comX, which encodes an alternative sigma factor called ComX. ComX is purported to activate all the late corn genes including all of the structural genes that are required for the bacteria to uptake and incorporate DNA.

Competence QS system and *S. mutans* Attachment

*Streptococcus mutans* ability to colonize the smooth surface of teeth is strongly enhanced in the presence of dietary sucrose. Although sucrose is used as a preferred fermentable carbon source, it is also the primary substrate of a group of glycosyltransferases. Amongst these enzymes is a group of three homologous glucosyltransferases (GTF) which are also necessary for efficient colonization (Loesche, 1986). All three GTFs transfer a glucose moiety from sucrose to a growing polysaccharide chain of glucose subunits (glucans). In addition, they all share at least 50% amino acid sequence identity, with GTFB and GTFC being greater than 75% identical.

All three GTFs function extracellularly and acquire their substrate, sucrose, from the oral cavity (reviewed in Banas and Vickerman, 2003). In addition, each GTF can be distinguished by the glycosidic linkage of its glucan product. GTFB forms primarily α-1-3 glucosidic linkages (mutan) that are insoluble while GTFD creates primarily α-1-6 glucosidic linkages (dextran) that are soluble. GTFC forms a mixture of both types of glucosidic linkages. While dextran is believed to be an important component of the biofilm-structure and can readily be metabolized by extracellular dextranases, mutan is believed to be essential for adherence and is very persistent, being a very poor metabolic substrate. Hence, the formation of mutan can be considered both a critical and committed step; one where sucrose a preferred carbon source is irreversibly utilized for attachment. Once initial attachment has occurred, specific adhesins are utilized for more permanent anchoring of the bacteria to the surface of the tooth. This obviates the need for further mutan production. (Goodman and Gao, 2000).

The gtfB and gtfC genes have coding sequences of 4.4 kb and 4.1 kb respectively. They are found in tandem repeat with only 198 bps separating their coding sequences; gtfD is unlinked. The former two genes are believed to be the product of gene duplication; this would account for their genetic arrangement and sequence similarity. The fact that the two coding sequences have been known to recombine under nonnative conditions to create a hybrid gene suggests that this tandem arrangement was intentionally retained for biological function.

One pathway of gtf regulation that has yet to be explored is through quorum sensing. It has been previously shown that gtfB and gtfC possess independent promoters but are both coordinately regulated in a growth phase dependent fashion; both gtfB and gtfC expression are strongly induced at low cell densities and strongly repressed at high cell densities (Goodman and Gao, 2000), the hallmark of QS.

In view of the foregoing discussion, it becomes clear that QS is important in the development of biofilms. Therefore, based on the discovery of the present invention, it becomes possible to develop strategies for controlling biofilm by disrupting the QS pathways.

Accordingly, in another aspect of the present invention, a method for treating or protecting against a condition associated with the attachment of *S. mutans* to teeth of a subject is provided.

A method according to this aspect of the present invention generally comprises the step of administering to the subject a composition containing CSP in an amount effective to reduce the presence of *S. mutans* on teeth, wherein the effective amount is dependent on the level of reduction desired based on a dose-response relationship between a growth rate of *S. mutans* and CSP.

Because sucrose may stimulate the growth of non-targeted bacteria, therefore, in some embodiments, the composition may further comprise sucrose. Alternatively, the composition may further comprise an orally acceptable carrier, an anticaries agent, or any other suitable dental care ingredients commonly used in the art.

Moreover, because it is an unexpected discovery of the present invention that an overdose of CSP may induce cell death, in some embodiments, the amount of CSP is preferably greater than 1 mg/ml.

A treatment or protection method according to the present invention has at least the following advantages. A method of the present invention is selective with respect to the target bacterium, and does not undesirably disturb the remaining microflora. The addition of sucrose will stimulate the growth of other non-targeted microbes to enhance the selective pressure against the targeted bacterium, providing a natural-selection based approach to eliminate the targeted bacterium, thereby, reducing the risk of side-effects associated with using a foreign compound. Furthermore, because QSM is a natural molecule produced by the bacterium, the likelihood of the bacterium developing a resistance is greatly reduced.

Other aspects and advantages of the invention will be apparent from the following detailed description and the appended claims.

BRIEF DESCRIPTION OF DRAWINGS

FIG. 2 is the peptide sequence of CSP using the one-letter amino acid abbreviation from amino terminus to carboxyl terminus.

FIG. 10 shows the putative ComE binding sites in the upstream regions of gftB and gftC.

DETAILED DESCRIPTION

Compositions

Figure 1:
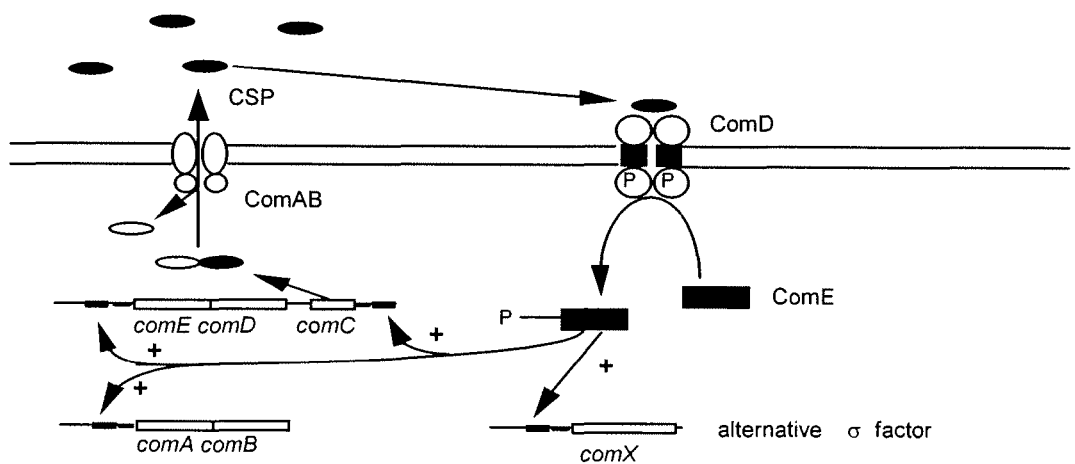
FIG. 1 is the postulated regulation of gtf genes by the competence pathway.

The compositions of this invention minimize the attachment of *S. mutans* to teeth, and thus minimize the negative consequences such as dental caries and endocarditis that can result from this attachment. Since other early colonizing oral bacteria rely on their own gtf genes for efficient adherence and are not affected by the presence of CSP, such non-pathogenic bacteria will gain a competitive advantage over *S. mutans*. In one embodiment, the composition comprises between about 0.05 and 30% (w/w) of CSP.

It is to be understood all peptides and proteins having the same or similar function as the CSP peptide encoded by the sequence shown in FIG. 2 (SEQ ID NO: 1) are considered to be functional equivalents of this peptide and are also included within the scope of this invention. Accordingly, the terms "*S. mutans* CSP" and "CSP" as used herein encompass the CSP of *S. mutans* and all functional equivalents thereof.

The CSP-containing compositions of this invention include sucrose. It was discovered that the negative effect of CSP on *S. mutans* is enhanced by the addition of sucrose. That is, since *S. mutans* is in direct competition with other early bacterial colonizers of the smooth surface of teeth and since many oral streptococci utilize similar glucosyltransferases to facilitate attachment, the combination of CSP and sucrose will specifically reduce the efficiency of *S. mutans* adherence while enhancing the ability of other non-pathogenic bacteria to more efficiently compete for the bare supergingival pellicle. Indeed, individuals that are edentate are devoid of *S. mutans*. Hence, CSP treatment should eventually lead to the surgical elimination of *S. mutans* from the oral cavity.

As used herein, the term "oral diseases" refers to diseases and disorders affecting the oral cavity or associated medical disorders that are caused by the attachment of *S. mutans* to a subject's teeth. Oral disorders include, but are not limited to, dental caries; periodontal diseases (e.g., gingivitis, adult periodontitis, early-onset periodontitis, etc.); mucosal infections (e.g., oral candidiasis, herpes simplex virus infections, oral human papillomavirus infections, recurrent aphtous ulcers, etc.); oral and pharyngeal cancers; and precancerous lesions.

The term "subject" refers to any animal, including mammals and humans.

The composition of this invention may further include one or more of anti-caries agents in addition to CSP. It is contemplated that various anti-caries reagents well known in the art can be included in the compositions and medicaments of the present invention and include, but are not limited to:

(1) substantially water insoluble noncationic antimicrobial agents, including but not limited to, Xylitol, triclosan, halogenated diphenyl ethers, benzoic esters; sesquiterpene alcohols (e.g., farnesol, nerolidol, bisabolol, and santalol), halogenated carbanilides, phenolic compounds including phenol and its homologs, mono-, poly-alkyl and aromatic halophenols, resorcinols (e.g., hexyl resorcinol), catechols (e.g., 2,2'-methylene bis (4-chloro-6-bromophenol), and bisphenolic compounds;

(2) non-steroidal anti-inflammatory drugs (NSAIDs), which can be characterized into five groups: (1) propionic acids (e.g., ibuprofen, indoprofen, ketoprofen, naproxen, benoxaprofen, flurbiprofen, fenoprofen, fenbufen, pirprofen, carpofen, oxaprozin, pranoprofen, miroprofen, tioxaprofen, suprofen, alminoprofen, tiaprofen, fluprofen, and bucloxic acid); (2) acetic acids (e.g., ketorolac, indomethacin, sulindac, tolmetin, zomepirac, diclofenac, fenclofenac, alclofenac, ibufenac, isoxepac, furofenac, tiopinac, zidometacin, acematacin, fentiazac, clidanac, oxpinac, and fenclozic acid); (3) fenamic acids (e.g., mefenamic acid, meclofenamic acid, flufenamic acid, niflumic acid, and tolfenamic acid): (4) biphenylcarboxylic acids (e.g., diflunisal and flufenisal); and (5) oxicams (e.g., piroxicam, sudoxicam and isoxicam);

(3) histidine-rich polypeptides ("HRPs," also referred to as histatins), such as histatin-based peptides disclosed in U.S. Pat. Nos. 4,725,576; 5,912,230; 5,885,965; 5,631,228; 5,646,119; and 5,486,503, each of which is incorporated herein by reference;

(4) fluoride reagents including sodium fluoride, stannous fluoride, amine fluorides, and monosodiumfluorophosphate;

(5) casein;

(6) plaque buffers such as urea, calcium lactate, calcium glycerophosphate, and strontium polyacrylates;

(7) non-immunogenic amino acid segments of proline-rich proteins that inhibit the adhesion of disease-causing microorganisms to tooth surfaces, as described in U.S. Pat. No. 5,013,542, incorporated herein by reference. The active ingredient can be derived from segmenting a natural or synthetic, proline-rich protein, to provide a non-immunogenic ingredient. The non-immunogenic amino acid segment can be obtained by various techniques, such as by cloning, or by synthesizing analogs of the natural molecules or their segments by chemical means. The non-immunogenic amino acid segment can also be obtained enzymatically or by cleaving the proline-rich protein derived from human saliva by the enzyme trypsin;

(8) antibodies against *S. mutans*, including intact molecules as well as functional fragments thereof, such as monoclonal IgG antibodies that specifically bind an antigen on the surface of *S. mutans*, including the following antibodies disclosed in U.S. Pat. No. 6,231,857, incorporated herein by reference: the hybridoma deposited with the American Type Culture Collection as ATCC No. HB12559 (designated SWLA1), the hybridoma deposited with the American Type Culture Collection as ATCC No. HB 12560, (designated SWLA2), and the hybridoma deposited with the American Type Culture Collection as ATCC No. HB 12258 (designated SWLA3). and (9) other pharmaceutically acceptable vehicles, diluents and additives such as antioxidants, buffers, bactericidal antibiotics and solutes which render the formulation isotonic in the intended recipient; and aqueous and non-aqueous sterile suspensions which may include suspending agents and thickening agents and liposome-based drug delivery systems commonly known in the art.

Oral Formulations

The compositions of this invention can be added to a variety of formulations suitable for delivery of the composition to the oral cavity, including, but not limited to, mouthwash solutions, abrasive dentifrice gels, nonabrasive dentifrice gels, denture washes or soaks, denture adhesives or cements, chewing gums, and soft drinks. In order to provide such formulations, a composition of this invention is combined with one or more orally acceptable carriers and/or excipients, or packed in a hydrophobic-delivery vehicle such as liposomes or any other hydrophobic delivery vehicle commonly known in the art. Formulations including, but not limited to, mouth washes, abrasive or nonabrasive dentifrices, chewing gums, soft drinks, and other orally acceptable compositions comprising CSP according to this invention can be prepared by any method known to persons skilled in the art. In general, methods of manufacturing anti-caries oral compositions comprise combining an orally acceptable carrier and an effective amount of CSP that can inhibit the expression of glucosyltransferases. An exemplary procedure for preparing an anti-caries oral composition in a gel formulation is provided in Example 9.

A variety of carriers and excipients can be used to formulate the compositions of this invention and are well known to those skilled in the art. Such orally acceptable vehicles for purposes of this invention include, but are not limited to, water, ethanol, humectants such as polypropylene glycol, glycerol and sorbitol, gelling agents such as cellulose derivatives (e.g., Methocel, carboxymethylcellulose (CMC 7MF) and Klucel HF), polyoxypropylene/polyoxyethylene block copolymers (e.g., Pluronic F-127, Pluronic F-108, Pluronic P-103, Pluronic P-104, Pluronic P-105 and Pluronic P-123), colloidal magnesium aluminosilicate complexes such as Veegum, and mucoprotein, thickening agents such as Carbopol 934, gel stabilizers such as silicon dioxides (e.g., Cab-O-Sil M5 and polyvinylpyrrolidone) sweeteners such as sodium saccharin and other approved flavors, preservatives such as citric acid, sodium benzoate, cetylpyridinium chloride, potassium sorbate, methyl and ethyl parabens, detergents such as sodium lauryl sulfate, sodium cocomonoglyceride sulfonate, sodium lauryl sarcosinate and polyoxyethylene isohexadecyl ether (Arlasolve 200), and approved colors.

Because human oral cavity contains saliva that is constantly being swallowed, therefore, an oral formulation preferably contains a sufficient amount of CSP to maintain an effective concentration of CSP in the oral cavity for a predetermined amount of time. Similarly, in other applications where the target environment may dilute the CSP to below effective amount, a higher concentration of CSP in the delivery vehicle is desired. For instance, an amount of CSP to account for dilution by saliva is preferably in the range of 0.1 mg/ml to 10 mg/ml.

Medicaments

Medicaments of this invention comprise CSP in an amount effective to reduce the attachment of S. mutans to teeth. An "effective amount" of CSP is the amount of compound that, when administered to a subject in need of treatment or prophylaxis, is sufficient to reduce the attachment of S. mutans to teeth and therefore, to treat or prevent conditions associated with the attachment of S. mutans to teeth. In one embodiment, the medicament comprises between about 0.05 and 30% (w/w) of CSP.

As used herein, the term "medicament" includes any type of medicament for administration to the oral cavity. In one embodiment the medicament can be a single dosage containing (1) CSP alone, (2) CSP in admixture with at least one additional agent effective against a condition associated with the attachment of S. mutans to teeth such as those described herein (3) CSP in admixture with sucrose, or (4) CSP in admixture with sucrose and at least one additional agent effective against a condition associated with the attachment of S. mutans to teeth.

Alternatively the medicament can be a kit with one or more dosage forms containing (1) CSP alone, (2) CSP and at least one additional agent effective against a condition associated with the attachment of S. mutans to teeth in admixture or in separate containers (3) CSP and sucrose in admixture or in separate containers, or (4) CSP, sucrose and at least one additional agent effective against a condition associated with the attachment of S. mutans to teeth, wherein the CSP, sucrose, and agent can be provided in separate vials or in admixture in any combination.

Method of Treatment

In general, dental caries and infective endocarditis may be prevented by contacting the oral cavity of a subject with an amount of S. mutans CSP effective to reduce or inhibit expression of the glucosyltransferase genes (gtfB and gtfC) either directly or indirectly, thereby reducing the attachment of S. mutans to the subject's teeth. In one embodiment, the CSP is formulated as an orally acceptable medicament as described herein comprising a carrier and an effective amount of CSP.

As used herein, the term "treating" is intended to mean at least the mitigation of a condition associated with the attachment of S. mutans to teeth in a subject, such as a human, that is affected at least in part by the condition, and includes, but is not limited to, modulating and/or inhibiting the condition; and/or alleviating the condition.

As used herein, the term "prophylaxis" is intended to mean at least preventing a condition associated with the attachment of S. mutans to teeth from occurring in a mammal, particularly when the mammal is found to be predisposed to having the condition but has not yet been diagnosed as having it.

With respect to treatment regime of CSP, whether alone or in combination with one or more additional anti-caries caries agents, one of ordinary skill in the art will recognize that a therapeutically effective amount will vary with the condition to be treated, its severity, the treatment regimen to be employed, the pharmacokinetics of the agent used, as well as the patient (animal or human) treated.

An exemplary regime of an anti-caries composition or medicament of this invention is application of the composition or medicament to the oral cavity of the subject every time the subject eats a food containing sucrose. For example, people generally eat foods with sucrose from one to three times a day. According to this embodiment, a subject would apply a composition or medicament of this invention to the oral cavity from one to three times daily soon after consuming a sucrose-containing food or beverage as part of a routine oral hygiene program to inhibit or treat dental caries or as a program to prevent endocarditis.

Since S. mutans is in direct competition with other early bacterial colonizers of the smooth surface of teeth and since many oral streptococci utilize similar glucosyltransferases to facilitate attachment, the presence of sucrose in any formulation of CSP should prove synergistic. Accordingly, the presence of sucrose in any CSP formulation or medicament of this invention will enhance the ability of glucosyltransferase dependent commensal bacteria to adhere. Thus, the combination of CSP and sucrose should both inhibit S. mutans attachment as well as facilitate the attachment of non-pathogenic bacteria, thus reducing the useable surface area and opportunity for S. mutans attachment. The plaque resulting from the attachment of non-pathogenic bacteria is benign and acts a barrier for subsequent S. mutans attachment.

The foregoing aspects and features of the invention are further illustrated by the results of the examples discussed below. The examples are not to be construed as limiting of the invention in anyway. Thus, various modifications are possible within the scope of the invention.

EXAMPLES

Materials and Methods

1) Cultures

The results were obtained using two strains of S. mutans: GS5, its derivative GS5-gtfBCD (Hanada, N, Kuramitsu, H. K., *Infection and Immunity*, 57:2079-2085 (1989)), NG8 and its derivative NG8-comC (Li, Y-H et al., *J. of Bact.* 183:897-908 (2001)). In each assay the corresponding wild-type strain was used as a control for each mutant. However, where ascertainable, no difference between the two wild-type strains namely NG8 and GS5 was observed. The bacteria were cultured in liquid or solid Todd Hewitt medium at 37° C. with 5% $CO_2$ without agitation. The horse serum was added to 5% where indicated.

2) Transcriptional Fusions

The fusion constructs and the transcription assay were previously described (Goodman, S. D. and Gao, Q., *Plasmid* 43:85-98 (2000)). Briefly, the constructs comprised the upstream regions of the gtfB and gtfC genes fused to the promoterless coding sequence of the firefly luciferase gene and inserted into the plasmid vector pVA838, a shuttle plasmid capable of propagating in both *E. coli* and *S. mutans* marked with erythromycin resistance. The plasmids were introduced into S. mutans GS5 by electroporation and the resulting erythromycin resistant strains were grown in liquid cultures and collected at various optical densities. The reporter gene (luciferase) expression was detected by measuring luminescence upon the addition of luciferin (the substrate for luciferase), see Goodman, S. D. and Gao Q. *Plasmid* 42:154-157 (1999), incorporated herein by reference.

3) Attachment Assay

The bacteria were grown in liquid cultures to the desired optical density. 20 ml of the cultures were then transferred into Petri dishes and sucrose added to the final concentration of 2%. The incubation was resumed for one hour, after which the liquid fraction was withdrawn and the fresh medium was added into which the layer of attached cells was scraped. The percentage of the attached bacteria was determined as the ratio of the optical densities of the attached to the total (a sum of attached and unattached) bacteria.

4) Competition Assay

The gtfBCD mutant (erythromycin-resistant) and the wild-type S. mutans were mixed at an initial ratio of 1:1000. The resulting liquid culture was grown to the optical density of 0.1 (the peak of GTF activity and maximum attachment). At this optical density 20 mL of the bacteria were placed into the Petri dish containing sucrose and allowed to attach. After one hour 10 mL (one half) of the unattached bacteria were transferred into another Petri dish, diluted 1:1 with fresh medium and allowed to attach. The dilutions assured that the culture maintains a high level of gtf expression characteristic of the low cell density. The transfer was performed a total of three times. After the final attachment period the free bacteria were collected, diluted and plated on solid medium to get individual colonies. The colonies were then picked and tested for erythromycin resistance by streaking on solid medium containing erythromycin. The ratio of sensitive and resistance colonies was calculated to determine the resulting ratio of the mutant to wild-type bacteria.

5) Western Blotting

For the Western blotting, the bacteria were incubated to the desired optical density, subjected to the freeze-thaw cycle and mixed with the sample loading buffer. The samples were heated at 100° C. for 15 minutes and subjected to the PAGE. The number of cells per lane of the gel was kept constant at $10^8$ cells. The western blotting was performed in accordance with a standard procedure (Sambrook, J. and Russel D. W. Molecular Cloning, a laboratory manual, $3^{rd}$ ed. Cold Spring Harbor Laboratory Press, NY, 2001). Briefly, after PAGE the samples were transferred onto the nitrocellulose membrane and the latter subjected to the standard ELISA procedure. The anti-GTFB mouse monoclonal antibody was previously characterized (Fukushima, K., Okada, T., Ochiai, K., *Infection and Immunity* 61:323-328 (1993), incorporated herein by reference). The secondary antibody (HRP-linked goat anti-mouse) and the detection reagents were purchased from Cell Signaling Technology (Beverly, Mass.).

6) Addition of CSP to Bacterial Cultures

Synthetic CSP was dissolved in water to the concentration of 1 mg/mL as described in Li, Y-H et al., *J. of Bact.*, 183: 897-908 (2001). The cultures were grown in Todd Hewitt Broth (THB) supplemented with 5% horse serum. CSP was added to the cultures at the time of diluting the overnight culture (time zero of the culture growth) to a designated concentration between 1 and 8 mcg/mL. The incubation then continued up to the optical density where the expression of GTF is maximal (OD 650=0.1). The cultures where then collected and used in Western blotting with anti-glucosyltransferase (gtf) antibody. A parallel Western blot was run with an anti-fructosyltransferase (ftf) antibody. The levels of FTF do not vary significantly during the growth of the culture. Cultures were also used for transcriptional fusion assays and for attachment assays.

7) Cloning and Expression of the S. mutans ComE Coding Sequence into E. coli

The DNA sequence of the comE gene is in the public domain and has a genbank accession number of AE015016.1. Oligonucleotides designed to be complimentary to the end points of the coding sequence were used to PCR amplify the intact coding sequence using S. mutans GS-5 chromosomal DNA as a template. The amplicon was then ligated into the Invitrogen (Carlsbad, Calif.) expression vector (pCR®T7TOPO®) according to the protocol of the manufacturer. In this genetic construction, comE is under the control of the plasmid's endogenous inducible promoter. E. coli strains either possessing the original plasmid or one with the new comE containing construction were grown to exponential growth and were treated with isopropylthiogalactoside which induces expression of the comE gene but only in this plasmid based system. After one hour of continued incubation, each culture was harvested, and lysed with lysozyme (0.4 mg/ml). Cell debris was pelleted by centrifugation and the remaining supernatant or cleared lysates were used for subsequent electromobility shift assays.

8) Electromobility Shift Assays with ComE Lysates

Electromobility shift assays (EMSA) were performed as described in Goodman et al., *J. of Bact.* 181:3246-3255 (1999). EMSA measures the extent of complexes formed at equilibrium between specific DNA sequences and proteins by the change in the rate of migration of the protein-DNA complex during gel electrophoresis as compared to the uncomplexed DNA. Complexed DNA migrates more slowly. For these experiments, a PCR DNA amplicon containing the promoter of gtfC and inclusive of the region from −89 to +103 (relative to the start of transcription designated as +1; the putative ComE site is located at −11 to +22) was used as the substrate for EMSA. Lysates of equivalent protein concentrations were used as the source of protein and added at 1:20 (v/v) to the reaction. Conditions for the formation of complexes and subsequent EMSA were performed as stated in Goodman et al., supra.

9) Techniques for detecting and quantitatively identifying S. mutans include bacterial culture with selective media using either broth or agar plate systems, and polymerase chain reaction techniques. (Ellen, R. P., *Oral Sci. Rev.* 8: 3-23 (1976); Igarashi et al., *Oral Microbiol. and Immunol.* 11: 294-298 (1996); U.S. Pat. No. 5,374,538; U.S. Pat. No. 4,692,407, each of which is incorporated herein by reference). Human dental caries may also be detected by changes in translucency, color, hardness or X-ray density of teeth. (U.S. Pat. No. 6,231,857, incorporated herein by reference).

Example 1

Figure 3:
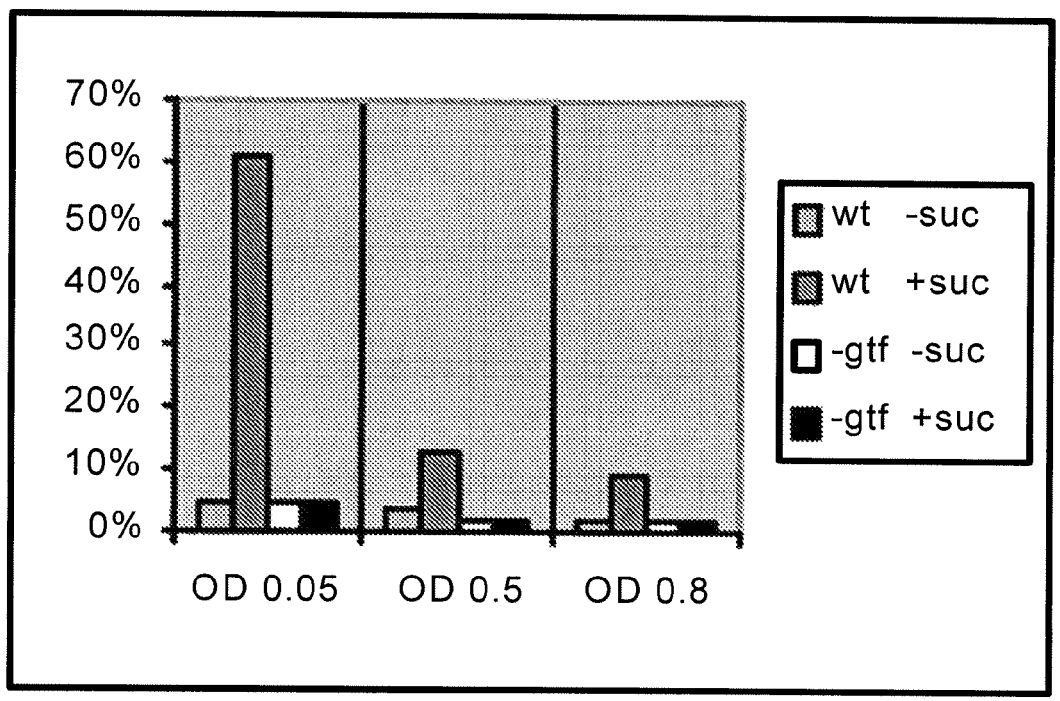
FIG. 3 shows the bar graph of the data from an in vitro attachment assay presented as the percentage of attached bacteria versus optical density of the total (attached and unattached) bacteria.

An in vitro assay was performed as described in Materials and Methods to determine whether glucosyltransferases and their substrate (sucrose) are required for the S. mutans attachment to a smooth surface. The results are shown in FIG. 3, which shows that glucosyltransferases and sucrose are required for the S. mutans attachment. It was observed that when sucrose was added to the medium, the wild-type S. mutans readily attached to the surface of a Petri dish. The attachment was evidenced by the clearance of the substantial number of bacteria from the liquid medium and the presence of the increasing number of bacteria in the mucous layer synthesized on the surface of the Petri dish. After an hour-long incubation, up to 60% of bacterial cells were localized to the layer. On the contrary, the gtf-deficient mutant of S. mutans formed no such layer and less than 5% of cells were cleared from the liquid medium. In addition, the data demonstrate that the ability to attach is maximal during late-lag phase, decreases to 10% by the mid-log phase and falls below 5% as the culture reaches the stationary phase.

Example 2

Figure 4:
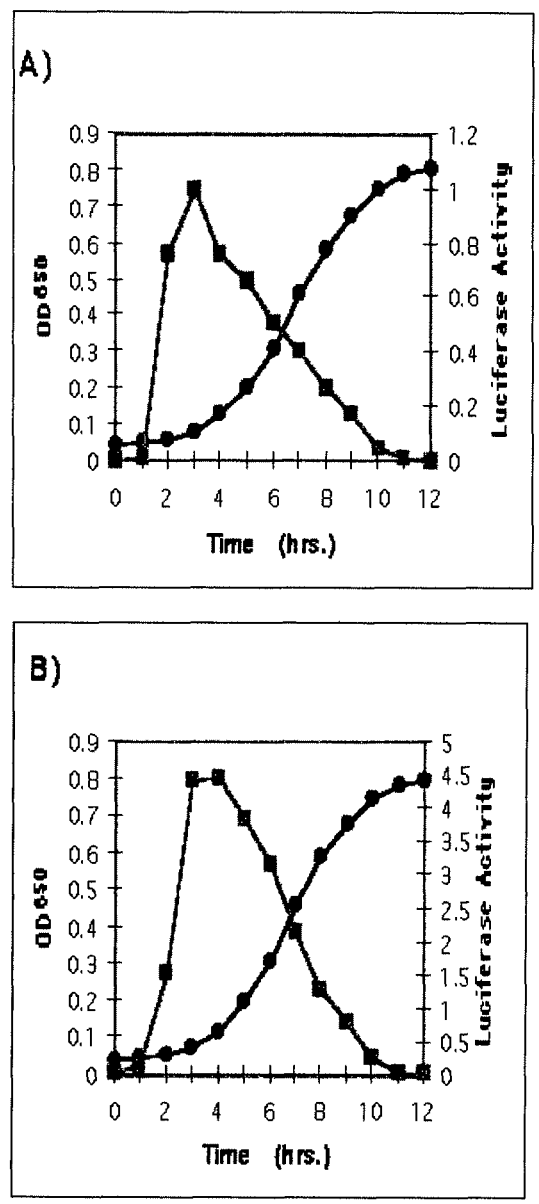
FIGS. 4A and 4B are graphs of the data from an in vivo transcriptional fusion assay of the growth phase-dependent expression of gftB (Panel A) and gftC (Panel B) genes in *S. mutans*, presented as optical density and luciferase activity versus time (hours).

A transcriptional fusion assay was performed as described in Materials and Methods. The results are shown in FIGS. 4A and 4B. After the S. mutans culture was diluted, the expression was low in the stationary phase but rose rapidly as bacteria progress through the lag phase. The gtfB and gtfC expression peaked at the end of the lag phase prior to the exponential growth. The expression declined dramatically during the phase of exponential growth and returned to the low levels when the *S. mutans* culture reached the stationary phase. In addition, the data show that the two genes have separate functional promoters but are nevertheless regulated in the similar fashion. This example demonstrates the growth phase-dependent expression of gtfB and gtfC genes in *S. mutans*. This pattern reflects the role of these genes in the early events in the life of an *S. mutans* culture (e. g., at the time of the initial colonization of a tooth surface).

Example 3

Figure 5:
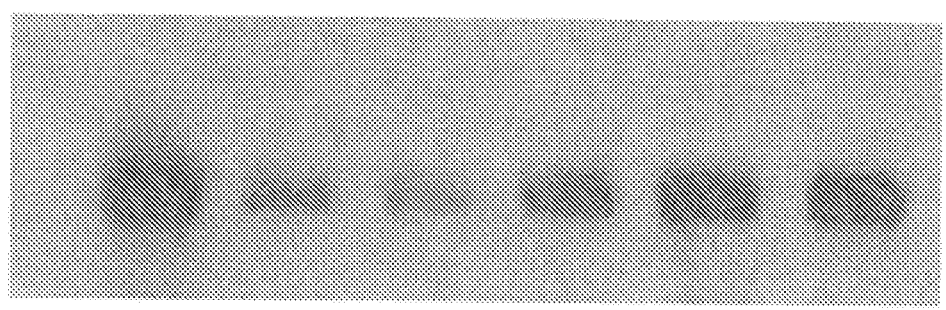
FIG. 5 is an image of a Western blot showing the overexpression of GTFB in the mutant of *S. mutans* lacking the CSP.

This example illustrates the role of CSP in regulating the gtfB gene. FIG. 5 is an image of a Western blot analysis using a monoclonal antibody against GTFB. As shown by FIG. 5, the normal pattern of GTFB expression is disrupted in the mutant *S. mutans* lacking the competence stimulating peptide (CSP). In the mutant *S. mutans*, the GTFB expression remained high throughout the growth of the culture. In contrast, in the wild-type, the amount of the protein was maximal in late lag phase and then dropped dramatically by the end of the exponential phase.

Example 4

Figure 6:
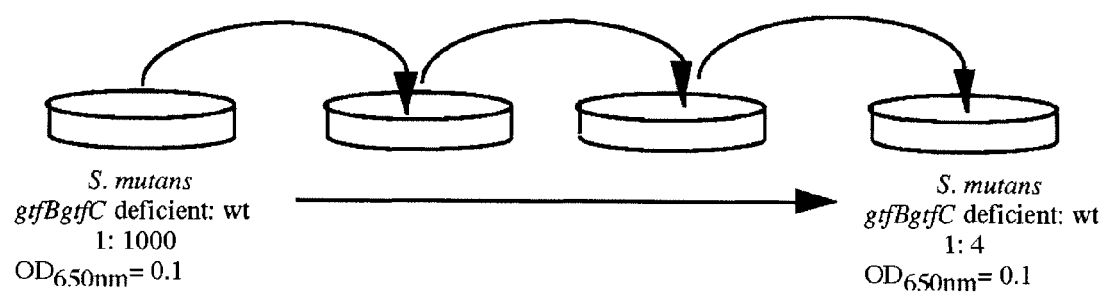
FIG. 6 is schematic representation of an in vitro attachment competition assay between the gftBCD (glucosyltransferase (gtf)-negative) mutant and wild-type *S. mutans*.

An in vitro competition assay was performed to demonstrate that the glucosyltransferase (gtf)-deficient mutant of *S. mutans* fails to attach to the surface in the presence of sucrose even when gtf-positive bacteria are present. The wild-type and mutant bacteria were mixed at an initial ratio of 1:1000. The unattached cells are periodically withdrawn and placed into a fresh dish. As shown in FIG. 6, after only three such passages the proportion of gtf-deficient bacteria in the supernatant increased 250-fold (from 1:1000 to 1:4). These results demonstrate that the GTF-expressing bacteria adhere to the surface while the GTF-deficient cells mostly remain in the liquid medium despite the fact that the glucans are available for attachment.

Example 5

Figure 7:
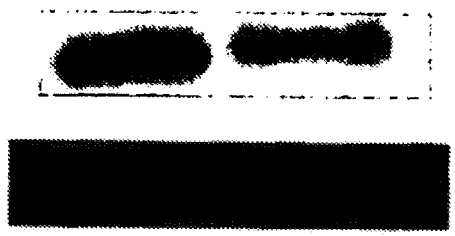
FIG. 7 is an image of a Western blot showing the negative effect of CSP on the GTFB expression in *S. mutans*.

A Western blot analysis was performed to determine the effect of CSP on the level of GTFB expression. As shown in FIG. 7, panel 1, CSP has a direct negative effect on the level of GTFB expression in the wild-type *S. mutans*. When CSP was added to the fresh cultures at the time of dilution, the peak expression of GTFB was lowered proportionally to the amount of peptide added. As a control, the same blot was analyzed with antibody specific to FTF, where it was observed that CSP has no effect on FTF expression (FIG. 7, panel 2).

Example 6

Figure 8:
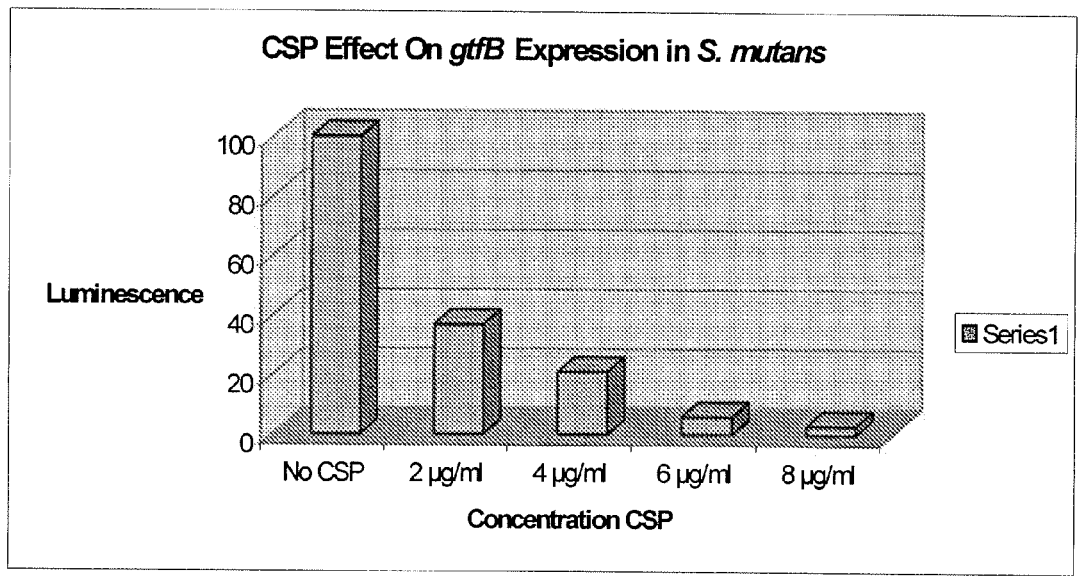
FIG. 8 is a bar graph of the data from a transcription fusion assay to determine the effect of CSP on gtfB gene expression in *S. mutans* presented as percent luminescence versus concentration of CSP.

The transcriptional fusion assay was performed to determine whether CSP inhibits the expression of the gtfB gene of *S. mutans*. *S. mutans* culture was first diluted from overnight cultures. The expression was low but rose rapidly as the bacteria progressed through the lag phase. When the expression peaked at the end of the lag phase prior to the exponential growth, the cells were challenged with increasing concentrations of CSP for an incubation period of 10 minutes and assessed for luminescence, the measure of reporter gene expression. As shown in FIG. 8, increasing concentrations of CSP increased the magnitude of repression. This example therefore demonstrates that CSP can inhibit the expression of at least the gtfB gene of *S. mutans*. The effect of CSP is consistent with repression at the level of transcription.

Example 7

Figure 9:
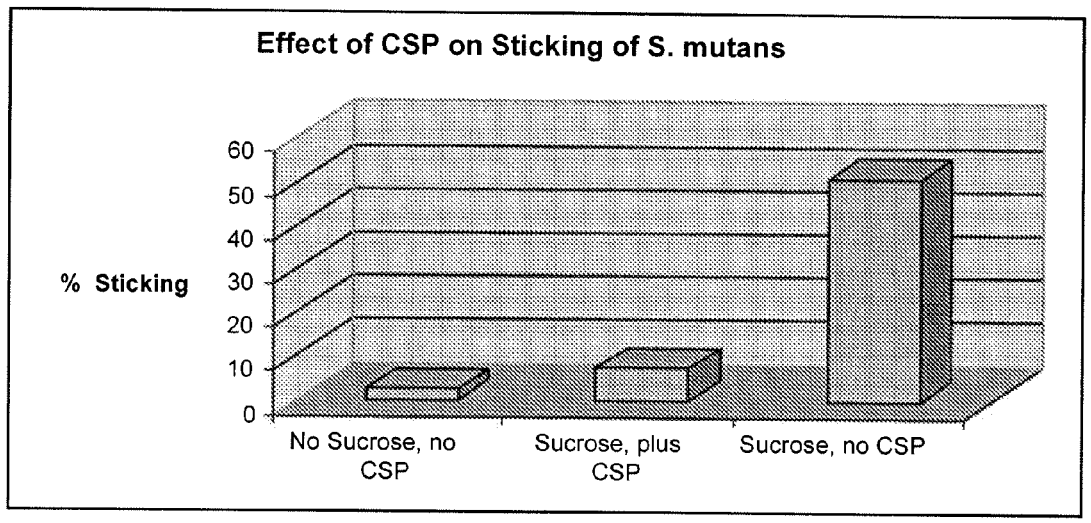
FIG. 9 is a bar graph of the percent of *S. mutans* that sticks to a surface in the presence of CSP and in the presence or absence of sucrose.

An in vitro assay was performed to determine whether CSP can inhibit the attachment of *S. mutans* to a smooth surface. When sucrose was added to the medium, the wild-type *S. mutans* readily attached to the surface of a Petri dish. The attachment was evidenced by the clearance of the substantial number of bacteria from the liquid medium and the presence of the increasing number of bacteria in the mucous layer synthesized on the surface of the Petri dish. *S. mutans* grown to an optical density consistent with the transition between lag and exponential growth for maximal expression of gtfB and gtfC was utilized. As shown in FIG. 9, after an hour-long incubation up to 51% of bacterial cells were localized to the layer. On the contrary, when bacteria were challenged with CSP at 8 □g/mL for 10 minutes prior to incubation on Petri dishes, *S. mutans* formed much less of a layer (less than 8%). This example therefore demonstrates that CSP can inhibit the attachment of *S. mutans* to a smooth surface.

Example 8

The putative regulatory pathway controlling the glucosyltransferase (gtf) gene expression is illustrated in FIG. 1. The competence stimulating peptide (CSP) is cleaved off of a larger peptide which is the product of the comC gene. CSP is extruded into the extracellular milieu by the specific transporter ComAB (the two components are the products of the genes comA and comB). The extracellular concentration of CSP increases with the increase in cell density. When the concentration reaches a threshold, CSP activates its specific receptor ComD. ComD in turn activates a response regulator ComE by phosphorylation. ComE modulates gene expression by binding to its target sites in the regulatory regions on the DNA. ComE regulator has been studied in a related species of the genus Streptococci: *S. pneumoniae*. In that system it has been shown that ComE interacts with its specific binding sites in the upstream regions of several genes and operons: comC, comX (an alternative sigma factor, a transcription factor), comAB, and comED. (Lee, M. S. and Morrison, D. A., *J. of Bact.*, 181:5004-5016 (1999)).

The inventors have shown that the putative ComE binding sites exist in the upstream regions of both gtfB and gtfC FIG. 10. In both gtfB and gtfC, promoter regions the ComE box can be found at −11 base of the promoter region. In FIG. 10, capital letters represent actual DNA sequence for gtfB and gtfC while they represent conserved sequence in a ComE consensus derived from the genus *streptococcus*. Lower case letters are less conserved DNA sequence. The letter W represents either an adenine or thymidine base pair. The asterisk (*) represents a potential one base pair gap in the DNA sequence alignment. This result points at the likelihood that CSP regulates gtf expression via the ComE pathway.

Figure 11:
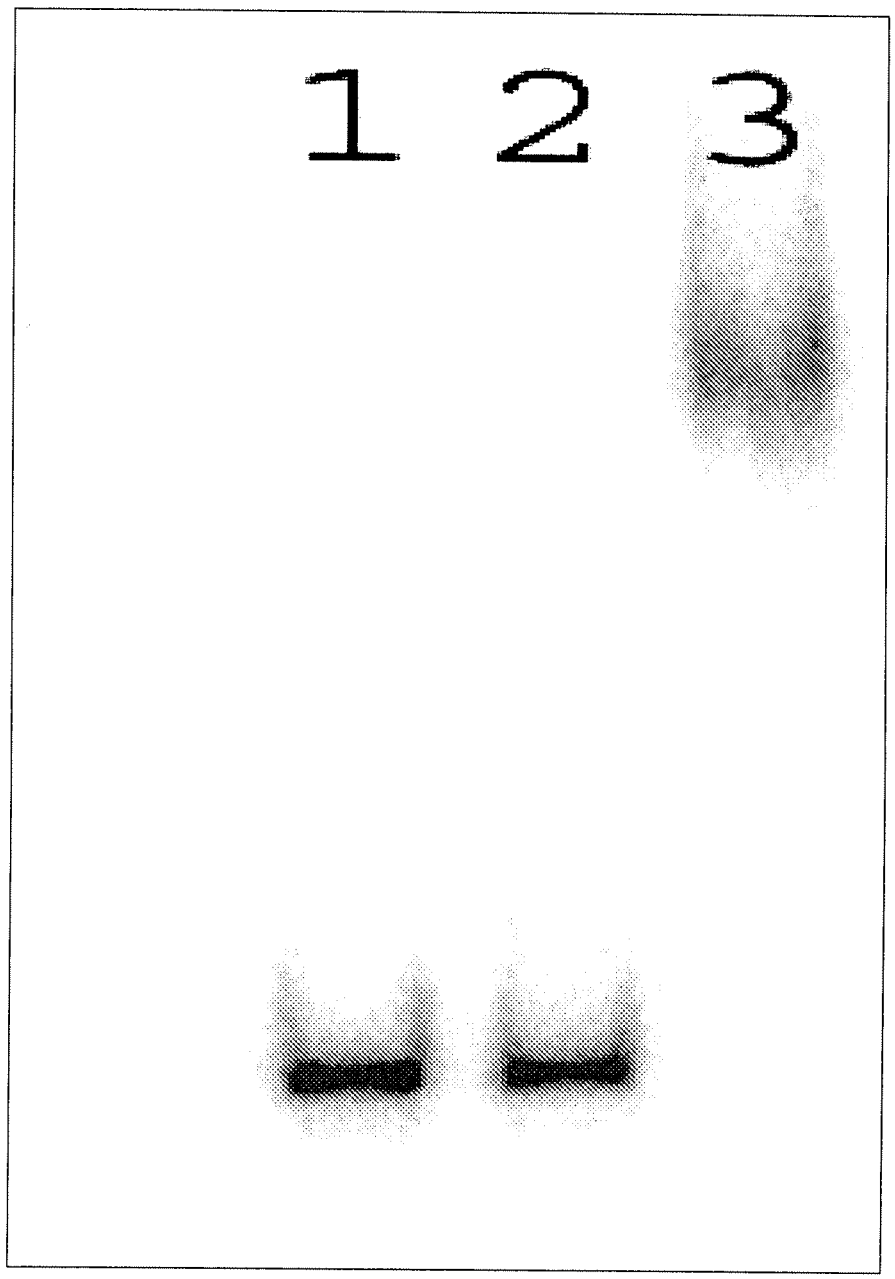
FIG. 11 is an image of an electromobility shift assay gel. Lane 1 is gtfC promoter DNA; Lane 2 is gtfC promoter DNA with *E. coli* cleared lysate added; and Lane 3 is gtfC promoter DNA with *E. coli* cleared lysate containing *S. mutans* ComE.

As evidence of this model, *E. coli* cleared lysates either possessing ComE or lacking ComE were used in an electromobility shift assay (EMSA) to assess the capacity of these lysates to bind to the gtfC promoter region that contains the streptococcal ComE box FIG. 11. Lysates that did not possess expressed ComE failed to form complexes with the gtfC promoter despite possessing a plethora of other *E. coli* proteins. It is believed that it is the ComE protein which is the only component that distinguishes these two lysates and creates the complex.

Example 9

This (tab) example provides an exemplary procedure for preparing a formulation comprising CSP according to this invention. Water, sodium saccharin, sodium benzoate and dyes are combined in a first container and the container is place in an ice bath. When the temperature reaches 6° C., a gelling agent is added. The contents are mixed slowly until the gelling agent is dissolved, and then the solution is heated to 70° C. Into a second container is added glycerin, and then Cab-O-Sil M5 is sprinkled in with mixing. CSP is then added and mixing is continued to a smooth paste. The paste is then heated in a water bath with mixing to a temperature of 70° C.

The contents of the first container are added to the second container and blended together until the batch is homogenous while maintaining a 70° C. temperature. A flavoring agent is then added, mixing is stopped, and the formulation allowed to settle for approximately one hour. If necessary, the formulation can be refrigerated overnight to remove air bubbles.

CSP can be produced in either of two ways. It is naturally secreted during exponential growth of *S. mutans*. Fermentation of the bacteria will result in the media being saturated with CSP. Spent or conditioned media can then be further purified or used directly. Alternatively, the peptide can be synthesized according to automated peptide synthesis procedures known in the art, such as the well known Merrifield method, as described in Merrifield, R. B. J. Am. Chem. Soc. 85:2149 (1963); and Merrifield, R. B. Science, 232:341 (1986), each of which is specifically incorporated herein by reference.

Example 10

This example provides an example of a mouthwash formulation according to this invention containing CSP.

| Ingredient | Amount (% w/w) |
| --- | --- |
| CSP | 0.5-2.0 |
| Glycerol (humectant) | 6.0 |
| Pluronic F-108 | 1.0 |
| Sodium saccharin (sweetener) | 0.3 |
| Deionized Water | q.s. |
| Flavors | 1.0 |
|  | 100.0 |

Example 11

This example provides another example of a mouthwash formulation according to this invention containing CSP.

| Ingredient | Amount (% w/w) |
| --- | --- |
| CSP | 0.5-3.0 |
| Ethanol, USP | 5.0 |
| Pluronic F-108 | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
|  | 100.0 |

Example 12

This example provides another example of an abrasive dentifrice gel formulation according to this invention containing CSP.

| Ingredient | Amount (% w/w) |
| --- | --- |
| CSP | 2.0-10.0 |
| Fumed Silica (abrasive) | 55.0 |
| Sodium Lauryl Sulfate (detergent) | 1.5 |
| Glycerol (humectant) | 10.0 |
| Carboxymethylecellulose (gelling agent) | 2.0 |
| Sorbitol (humectant) | 10.0 |
| Sodium saccharin (sweetener) | 0.2 |
| Deionized Water | q.s. |
| Perservative | 0.05 |
| Flavors | 1.0 |
|  | 100.0 |

Example 13

This example provides an example of a chewing gum formulation according to this invention containing CSP.

| Ingredient | Amount (% w/w) |
| --- | --- |
| CSP | 1.0-11.0 |
| Gum Base | 21.3 |
| Sucrose | 48.5-58.5 |
| Corn Syrup (Baume 45) | 18.2 |
| Flavors | 1.0 |
|  | 100.0 |

Example 14

This example provides an example of a nonabrasive gel dentifrice formulation according to this invention containing CSP.

| Ingredient | Amount (% w/w) |
| --- | --- |
| CSP | 0.05-30.0 |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium Saccharin | 0.2 |
| Flavors | 1.5 |
|  | 100.0 |

Example 15

This example provides another example of a nonabrasive gel dentifrice formulation according to this invention containing CSP.

| Ingredient | Amount (% w/w) |
| --- | --- |
| CSP | 5.0 (dry basis) |
| Distill water | q.s. |
| Sodium Saccharin (sweetener) | 0.20 |
| Sodium Benzoate (preservative) | 0.30 |

-continued

| Ingredient | Amount (% w/w) |
|---|---|
| FD&C Blue #1 (0.1% aq. soln.) | 0.27 |
| D&C Yellow #10 (0.5% aq. soln.) | 0.50 |
| Gelling agent | 18.00 |
| Glycerol (Humectant) | 20.00 |
| FCab-O-Sil M5 (Silicon Dioxide) | 1.0 |
|  | 100.0 |

Example 16

This example provides an example of a soft drink formulation according to this invention containing CSP.
Ingredient
Distilled Water
Carbon Dioxide
Sucrose
Flavors
Colors
Caffeine
Acidulants
Preservatives
Potassium
Sodium
CSP Example 17

This example provides an example of a candy formulation according to this invention containing CSP.
Ingredient
Distilled Water
Leavening agents
Stabilizers
Thickeners
Sucrose
Flavors
Colors
Acidulants
Preservatives
Antioxidants
CSP Example 18

This example shows the dose-dependent response of *S. mutans*' growth rate versus the amount of CSP administered.

Figure 12:
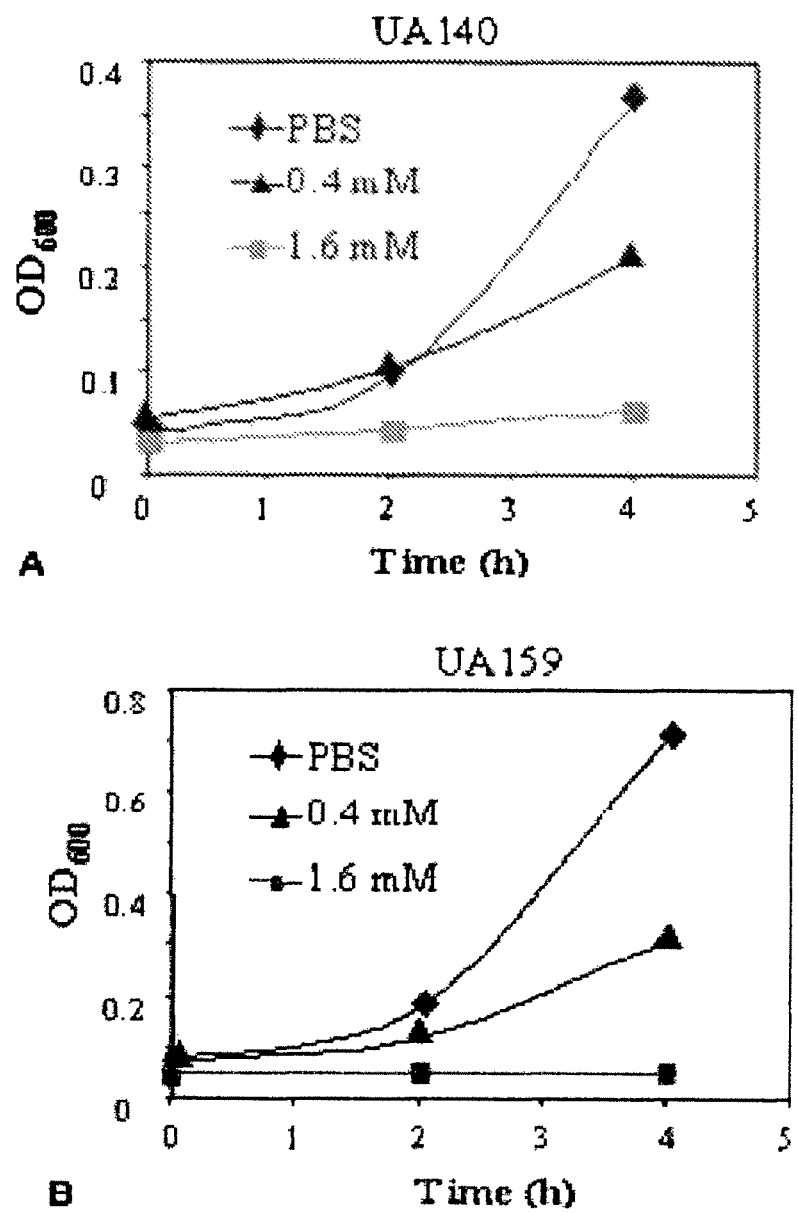
FIG. 12 shows temporary growth inhibition of *S. mutans* wild-type strains UA140 (A) and UA159 (B) by CSP.

Previously, it was assumed that quorum sensing may be an on/off type of switching event wherein when the quorum sensing molecule reaches a certain threshold, a new behavior is turned on and vice versa. The inventors have unexpectedly discovered that the QS regulated gene expression is not an all-or-nothing type of system, but actually has a dose-dependent response. The inventors have demonstrated in this example that at higher concentrations of CSP, the growth of the *S. mutans* culture slowed down. At 8 μg/ml (4 μM) we see the desired inhibition of the gtf genes. At a 100-fold higher concentration (400 μM), CSP inhibits the growth of a *S. mutans* culture by 50%. At a 400-fold higher concentration (1.6 mM) the cell division stops and cells begin to die (see FIG. 12). The microscopic observation of the culture treated with high concentrations of CSP revealed some overly large cells. This suggested that CSP inhibited cell fission. The live-dead stain further demonstrated that the overly large cells were dead.

The experiment was performed in a 96-well plate with triplicate wells for each treatment. Cell density was measured by using a plate reader (BioRad). The experiment was repeated three times. Numbers represent the average of the triplicate samples from one representative experiment. Variations between experiments were within 20%.

These experiments were designed to mimic the conditions of the dental hygiene regimen. Specifically, the bacteria were "pulsed" with CSP. The peptide was added for a mere 10 minutes, washed away and the incubation continued in the fresh medium. In this set-up the inhibitory effect persisted for a long time and became undetectable only after 16 hours of the culture growth. Competition experiments have also shown that a mere 3-hour advantage is sufficient to ensure that a resident species in a biofilm will out compete the newcomer.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A method for treating a condition associated with the attachment of *Streptococcus mutans* to teeth of a subject, comprising:
administering to the subject a composition comprising an orally acceptable carrier in combination with a competence stimulating peptide in an amount effective to inhibit the expression of at least one glucosyltransferase gene selected from the group consisting of gftB and gftC, thereby reducing the presence of *Streptococcus mutans* on the teeth of the subject, wherein the effective amount is dependent on the level of reduction based on a dose-response relationship between a growth rate of *Streptococcus mutans* and the competence stimulating peptide, and wherein the competence stimulating peptide comprises SEQ ID NO: 1.

2. The method of claim 1, wherein the composition further comprises an anti-caries agent.

3. The method of claim 1, wherein the composition is in the form of a mouthwash solution, an abrasive dentifrice gel, a chewing gum, a nonabrasive dentifrice gel, a nonabrasive gel composition, or a soft drink.

4. The method of claim 1, wherein the condition is selected from a group consisting of dental caries and infective endocarditis.

5. The method of claim 2, wherein the anti-caries agent is selected from the group consisting of water insoluble noncationic antimicrobial agents, non-steroidal anti-inflammatory drugs, fluoride reagents, histidine-rich polypeptides, casein, urea, calcium lactate, calcium glycerophosphate, non-immunogenic amino acid segments of proline-rich proteins, and monoclonal antibodies against *Streptococcus mutans*.

6. The method of claim 1, further comprising the step of cleaning the teeth before the administering step.

7. The method of claim 1, wherein the amount of the competence stimulating peptide is greater than 1 mg/ml.

8. The method of claim 1, wherein the competence stimulating peptide is packaged in a hydrophobic delivery vehicle and the composition further comprises one or more competence stimulating peptide stabilizing agents.

9. The method of claim 8, wherein the competence stimulating peptide stabilizing agents are selected from the group consisting of a detergent, a hydrophobic solvent, and combinations thereof.

10. A method for treating a condition associated with the attachment of *Streptococcus mutans* to teeth of a subject, comprising:

administering to the subject a composition comprising an orally acceptable carrier in combination with a competence stimulating peptide in an amount effective to reduce the presence of *Streptococcus mutans* on the teeth of the subject, wherein the competence stimulating peptide comprises SEQ ID NO: 1.

11. The method of claim 10, wherein the composition further comprises an anti-caries agent.

12. The method of claim 10, wherein the composition is a mouthwash solution, an abrasive dentifrice gel, a chewing gum, a nonabrasive dentifrice gel, a nonabrasive gel composition, or a soft drink.

13. A method for treating a condition associated with the attachment of *Streptococcus mutans* to teeth of a subject, comprising:

administering to the subject a composition consisting essentially of an orally acceptable carrier in combination with a competence stimulating peptide in an amount effective to reduce the presence of *Streptococcus mutans* on teeth, wherein the effective amount is dependent on the level of reduction based on a dose-response relationship between a growth rate of *Streptococcus mutans* and the competence stimulating peptide, and wherein the competence stimulating peptide comprises SEQ ID NO: 1.

14. The method of claim 13, wherein the composition further comprises an anti-caries agent.

15. The method of claim 13, wherein the composition is in the form of a mouthwash solution, an abrasive dentifrice gel, a chewing gum, a nonabrasive dentifrice gel, a nonabrasive gel composition, or a soft drink.

16. The method of claim 13, wherein the composition is in the form of a mouthwash solution, an abrasive dentifrice gel, a chewing gum, a nonabrasive dentifrice gel, a nonabrasive gel composition, or a soft drink.

17. The method of claim 13, wherein the condition is selected from a group consisting of dental caries and infective endocarditis.

18. A method of inhibiting expression of at least one glucosyltransferase gene selected from the group consisting of gftB and gftC in *Streptococcus Mutans* comprising the step of contacting *Streptococcus mutans* with a competence stimulating peptide, wherein the competence stimulating peptide comprises SEQ ID NO: 1.

* * * * *

SEQUENCE LISTING

<160> NUMBER OF SEQ ID NOS: 1

<210> SEQ ID NO 1
<211> LENGTH: 21
<212> TYPE: PRT
<213> ORGANISM: Streptococcus mutans

<400> SEQUENCE: 1

Ser Gly Ser Leu Ser Thr Phe Phe Arg Leu Phe Asn Arg Ser Phe Thr
1               5                   10                  15

Gln Ala Leu Gly Lys
            20